(12) United States Patent
Hesse

(10) Patent No.: US 6,993,112 B2
(45) Date of Patent: Jan. 31, 2006

(54) DEVICE FOR PERFORMING AND VERIFYING A THERAPEUTIC TREATMENT AND CORRESPONDING COMPUTER PROGRAM AND CONTROL METHOD

(75) Inventor: Bernd-Michael Hesse, Mossautal (DE)

(73) Assignee: Deutsches Krebsforschungszentrum Stiftung des Oeffentlichen Rechts, Heidelberg (DE)

( * ) Notice: Subject to any disclaimer, the term of this patent is extended or adjusted under 35 U.S.C. 154(b) by 0 days.

(21) Appl. No.: 10/506,966

(22) PCT Filed: Mar. 12, 2002

(86) PCT No.: PCT/EP02/02693

§ 371 (c)(1),
(2), (4) Date: Sep. 8, 2004

(87) PCT Pub. No.: WO03/076016

PCT Pub. Date: Sep. 18, 2003

(65) Prior Publication Data
US 2005/0152495 A1 Jul. 14, 2005

(51) Int. Cl.
*A61N 5/10* (2006.01)

(52) U.S. Cl. ............................................ 378/65; 378/64
(58) Field of Classification Search ............ 378/64–65; 250/492.2, 492.22, 492.3; 600/427
See application file for complete search history.

(56) References Cited

U.S. PATENT DOCUMENTS

| 4,726,046 A | 2/1988 | Nunan |
| 5,233,990 A * | 8/1993 | Barnea ....................... 600/427 |
| 5,278,886 A | 1/1994 | Kobiki |
| 5,471,516 A | 11/1995 | Nunan |
| 5,538,494 A | 7/1996 | Matsuda |
| 5,778,043 A | 7/1998 | Cosman |
| 5,825,845 A | 10/1998 | Blair |

(Continued)

FOREIGN PATENT DOCUMENTS

WO WO 00 07 669 2/2000

(Continued)

OTHER PUBLICATIONS

David A. Jaffray, Ph.D. et al.. "A Radiographic and Tomographic Imaging System Integrated into a Medical Linear Accelerator for Localization of Bone and Soft-Tissue Targets". Int. J. Radiation Oncology Biol. Phys., vol. 45, No. 3, pp. 773-789, 1999.

(Continued)

*Primary Examiner*—David V. Bruce
*Assistant Examiner*—Hoon Song
(74) *Attorney, Agent, or Firm*—Paul Vincent

(57) ABSTRACT

The invention relates to a device for performing and verifying therapeutic radiation. An x-ray beam (4) is arranged across from a target volume (3) of the beam source (11) for the high-energy beam (1) in such a way that the beams (1, 4) run in essentially opposite directions (5, 6). The invention also relates to a computer program and a control method for operating said device. The inventive device makes it possible to exactly verify areas (16, 16', 16") that are subjected to different levels of radiation, the entire anatomy of the target volume (3), and the surroundings thereof in addition to the contour of the therapy beam (1). The x-ray beam (4) detects the anatomy and position of the patient (21) within the range of the target volume (3) before the high-energy beam (1) is applied and the shape of the applied high-energy beam (1) is then detected and areas (16, 16', 16") that are subjected to different levels of radiation as well as at least one partial segment of the target volume (3) during the emission breaks of the high-energy beam (1). The detected data is used for correcting the treatment plan.

25 Claims, 3 Drawing Sheets

U.S. PATENT DOCUMENTS 6,198,957 B1     3/2001    Green
6,307,914 B1    10/2001    Kunieda

FOREIGN PATENT DOCUMENTS

WO      WO 02 22 210      3/2002

OTHER PUBLICATIONS

T. Rock Mackie et al.. "Tomotherapy: A new concept for the delivery of dynamic conformal radiotherapy", Med. Phys. 20(6), Nov./Dec. 1993, p. 1709 ff.

* cited by examiner

DEVICE FOR PERFORMING AND VERIFYING A THERAPEUTIC TREATMENT AND CORRESPONDING COMPUTER PROGRAM AND CONTROL METHOD

This application is the national stage of PCT/EP02/02693 filed on Mar. 12, 2002.

BACKGROUND OF THE INVENTION

The invention concerns a device for performing and verifying therapeutic radiation, comprising a radiation source for a high-energy beam and a means for modulation of the high-energy beam on the gantry of an irradiation device, wherein for verification, an X-ray beam is disposed across from a radiation source for high energy beams and opposite a target volume of the radiation source for those high-energy beams such that the rays extend substantially oppositely to each other, and with a medium for detecting the X-ray beam disposed, relative to its radiation direction, behind the target volume and a medium for detecting the high-energy beam disposed, relative to the direction of this ray, before the target volume. The invention also concerns a computer program and a control method for operating this device.

A device of this type is disclosed in U.S. Pat. No. 5,233,990. In this device, the therapeutic beam and the X-ray beam are imaged on a screen, to permit determination as to whether or not the delimitation of the therapeutic ray by shielding blocks corresponds with the imaged X-ray image of the target volume. This document also discloses a corresponding method for controlling this device and mentions the possibility of using a computer program. This device only permits comparison of the outer contours of the therapeutic ray with the outer contours of the target volume. Spatial detection, detection of the treatment intensity of regions to be irradiated with different intensities and detection of the anatomy of the irradiation surroundings are not possible. The intensity and the surroundings, however, provide important information if structures with low contrast, such as e.g. a tumor and endangered organs, are close to each other. This requires exact verification that the treatment zone corresponds with the position and anatomy of the target volume while avoiding critical target volume surroundings.

It is therefore the underlying purpose of the invention to provide radiation treatment which, in addition to the contour of the therapeutic ray, also permits exact verification of regions of various radiation intensities and of the entire three-dimensional anatomy of the target volume and its surroundings, in particular, including bordering endangered organs.

SUMMARY OF THE INVENTION

This object is achieved with a device of the above-mentioned type, in that the medium is designed for detecting regions of various radiation doses of the high-energy beam, with a controller being connected to the media for detecting the radiation, to the means for modulation of the high-energy beam, to a drive for adjusting the position of the patient table, and to the radiation sources, wherein the controller is programmed with a treatment plan and designed to control the gantry and the above-mentioned elements in such a manner that a) before application of the high-energy beam, the anatomy and position of the patient in the region of the target volume are spatially detected by the X-ray beam by directing same onto this region from various directions, b) the detected anatomy and position of the patient are compared with the treatment plan and the patient position and/or the treatment plan are corrected, if necessary, c) the high-energy beam is applied from a first direction and thereby detected with respect to its shape and regions of varying radiation doses, d) at least one partial region of the target volume including its immediate vicinity is detected by the X-ray beam during a transmitting break of the high-energy beam, e) the x-ray recording is compared with the detected, applied high-energy beam and the treatment plan is corrected, if necessary, f) the steps c), d), and e) are repeated until the irradiation prescribed by the treatment plan for the first irradiation direction is achieved, g) steps c) through f) are repeated for all irradiation directions provided in the treatment plan. The inventive computer program is designed to enable control of the device to carry out the above-mentioned functions. It may be stored in a permanent storage location of the controller or be made available for control through a data carrier or online. The control method also serves for operation of the inventive device.

The inventive device and the inventive computer program and control method permit basing the performance and verification of a therapeutic radiation treatment plan through determination of irradiations in three-dimensional space.

In a first step, the X-ray detects whether the patient is positioned in accordance with this three-dimensional plan, wherein the position as well as the instantaneous anatomy of the patient can be detected, examined and corrected through detection from different directions using the X-ray beam. In case of substantial variations, it is, of course, also possible to restart treatment at a later point in time after such correction.

In the subsequent processing steps, transmitting breaks in the high-energy beam—which are always present in pulsed beams—are utilized to examine the above-mentioned features and to perform continuous correction and examination within intervals which are sufficiently short that even short-term anatomic changes, caused e.g. by the heart beat and breathing or muscle flexations, can be taken into consideration. This examination is performed many times for each individual treatment direction of the therapeutic beam such that erroneous irradiation can be largely excluded.

For this examination, the invention provides that at least one partial region of the target volume, including its immediate vicinity, is detected by the X-ray beam during the transmitting breaks of the therapeutic beam. To be able to effect correction as quickly as possible, i.e. even during the treatment cycle immediately following the break, only a critical region may be detected, verified, and corrected. Such a critical region could e.g. be a tumor edge which borders on an endangered region such as the spinal cord. In this case, the region of the tumor edge and the edge of the spinal cord must be examined and corrected with particular care and accuracy.

The varying radiation doses for different regions of the target volume are, in particular, also detected and compared with the current position and anatomy and, if necessary, the treatment plan is corrected in three-dimensional space. This examination may also include the region around the target volume which is compared with the treatment plan and is constantly taken into consideration for verification and correction. In particular, the entire treatment volume must be observed i.e. all tissue penetrated by the rays. The endangered organs must be taken into consideration to keep their exposure below a defined radiation dose. This radiation dose and monitoring of the surroundings is, in particular, important in the vicinity of vital organs, the irradiation of which must be minimized.

It is essential for the invention that these examinations and corrections are based on the three-dimensional information detected in the first step, thereby providing much more accuracy compared to purely two-dimensional comparison proposed by the above-mentioned prior art.

The following further developments concern the inventive device, the computer program and the control method for operating the invention. These are preferably designed such that permanent verification is based on three-dimensional detection of the region of the target volume in real time. The term "real time" means that the region of the target volume is detected in three dimensions not only before treatment but also during treatment. This is possible in that the X-ray beam is directed, during transmitting breaks, onto at least one partial region of the target volume including its immediate vicinity from different directions, but within a sufficiently small region that it is substantially still opposite to the direction of radiation of the high-energy beam to also detect, via data collected from various directions, the above-mentioned detection region in three dimensions and take it into consideration for verification in real time.

These different directions can be determined and technically realized in different ways. In one embodiment, the radiation source is designed such that the X-ray beam describes a circular motion in one plane which is disposed around an axis extending through the target volume and towards the radiation source of the high-energy beam. To be able to process this data, the corresponding control method and a computer program are required which are designed for evaluation of the X-ray acquisition data. The circular motion may be exercised by a corresponding mechanical device, e.g. using a rotary disc.

As mentioned above, it is of particular importance that the shape and position of endangered organs is taken into consideration for verification and correction of the modulation of the high-energy beam. The controller, the method and the computer program for carrying out the control must be designed accordingly. Towards this end, the invention provides particular advantages compared to conventional devices and methods, since spatial detection and verification considerably reduces the danger of substantial damage due to changes in position and anatomy. To be able to perform the above-mentioned verification in minimum time thereby taking into consideration a three-dimensional instantaneous recording, the X-ray beam can detect a partial region of the target volume including a bordering region of an endangered organ during the transmitting breaks in the high-energy beam, and this detection is taken into consideration for verification in real time. This limits the processed data to the critical region, considerably reducing its amount while still providing continuous exact examination in three-dimensional space where required.

A protocol about the applied radiation, preferably in three-dimensional space, and/or a protocol about the corrections of the treatment plan for the performed application of radiation are advantageously produced.

The above-mentioned features can be realized in the form of a device, a computer program or a control method. The computer program is, of course, only one preferred embodiment of a machine control sequence which is designed to be performed mechanically by the controller. It could also be designed as hardware or be carried out mechanically in another manner.

In an advantageous further development of the device, both media for detecting the high-energy beam and for detecting the X-ray beam are designed as one common medium. In this manner, one detection medium is omitted and the overall number of devices is reduced. Association of the two detections is also simplified. The individual detection elements can thereby also be used for detecting both beams by e.g. detecting the X-ray beam directly on the surface and the therapeutic beam during penetration through the medium. The medium must consist of a material which is not damaged by the energetic therapeutic beam. The medium may e.g. be an array of photo diodes, which consist of an amorphous material, e.g. amorphous silicon or amorphous selenium. The beams cannot thereby destroy a lattice structure. The photo diodes should also be disposed in a housing which minimally attenuates the high-energy beam such that processing is not subject to differences which would be relevant to the treatment. The photo diodes could e.g. be disposed in a plastic housing which would prevent any noticeable weakening or scattering of radiation.

The following discussion with reference to the drawing serves to explain the invention.

DESCRIPTION OF THE PREFERRED EMBODIMENT

Figure 1:
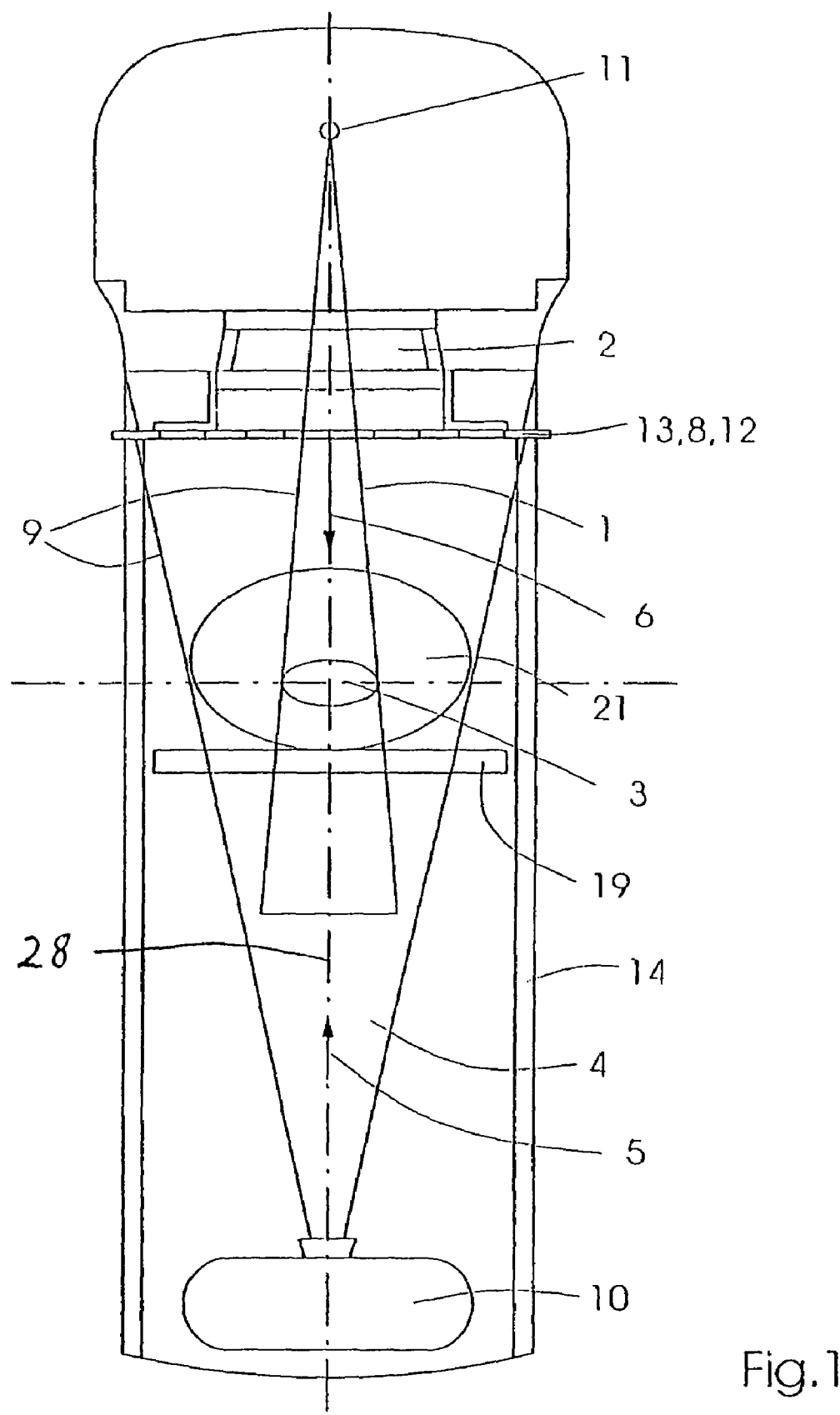
FIG. 1 shows a schematic diagram of an embodiment of the inventive device.

FIG. 1 shows the principle of the invention using an embodiment of the inventive device. A high-energy beam 1 is generated by a radiation source 11 and modulated by a means for beam modulation 2, e.g. a multileaf collimator, in accordance with the treatment plan, and directed onto a target volume 3. This is generally a tumor of a patient 21 who is lying on a patient table 19. In accordance with the invention, a medium 8 for detecting the high-energy modulated beam 1 with respect to its shape and regions 16, 16', 16" of different radiation doses (FIG. 3) is disposed in the path of rays 9 between the means 2 for radiation modulation and the patient 21, such that the shaping and intensity modification of the device 2 for radiation modulation can be detected and monitored. If the modulation of the ray 1 differs from its desired value, switching off or correction-may follow.

A radiation source 10 for an X-ray beam 4 is disposed opposite to the radiation source 11 for the high-energy beam 1 such that a path of rays 9 is generated, in which the direction 5 of the X-ray beam 4 is substantially opposite to the direction 6 of the high-energy beam 1. The X-ray beam 4 serves to detect the target volume 3 and the anatomy and position of the patient 21 in the manner described above. A medium 12 detects the X-ray beam 4 after its passage through the patient 21. The media 8 and 12 are suitably designed as medium 13 for detecting the high-energy beam 1 and the X-ray beam 4. Reference is made to the above-mentioned embodiments with regard to suitable design.

The radiation sources 11 and 10 are arranged such that the therapeutic beam 1 irradiates the target volume 3 and the X-ray beam 4 detects the target volume 3 and its surroundings which should also be taken into consideration for modulation of the therapeutic beam 1. For this reason, the X-ray beam 4 is more divergent than the therapeutic beam 1. The X-ray beam 4 may, of course, be narrower than shown and must not detect the entire patient 21.

If a detection medium 13 is provided, its surface must be dimensioned such that it detects the conically diverging rays 1 and 4 in the position of the arrangement of the detecting medium 13.

The treatment is suitably carried out with the following steps:

In a first step of the verification procedure, a current computer tomography data set of the patient 21 in the therapeutic situation is obtained directly before start of the radiation therapy using a computer tomography system i.e. the X-ray beam 4 and a medium 12 or 13. Changes of the target region 3 and position errors of the patient 21 can be directly recognized such that the subsequent therapy can be matched with this new data. The target region 3 and its surroundings are detected several times from various directions 7 (see FIG. 3), wherein these directions 7 are obtained through rotation of the gantry 14 to various positions. Using the data obtained in this manner, a controller (FIG. 2) can produce a three-dimensional image of the target volume 3 and its surroundings and compare it with a previously established, stored three-dimensional treatment plan. The position of the patient 21 can then be corrected e.g. through adjustment motions of the patient table 19 (FIG. 2) or through correction of the treatment plan.

Figure 3:
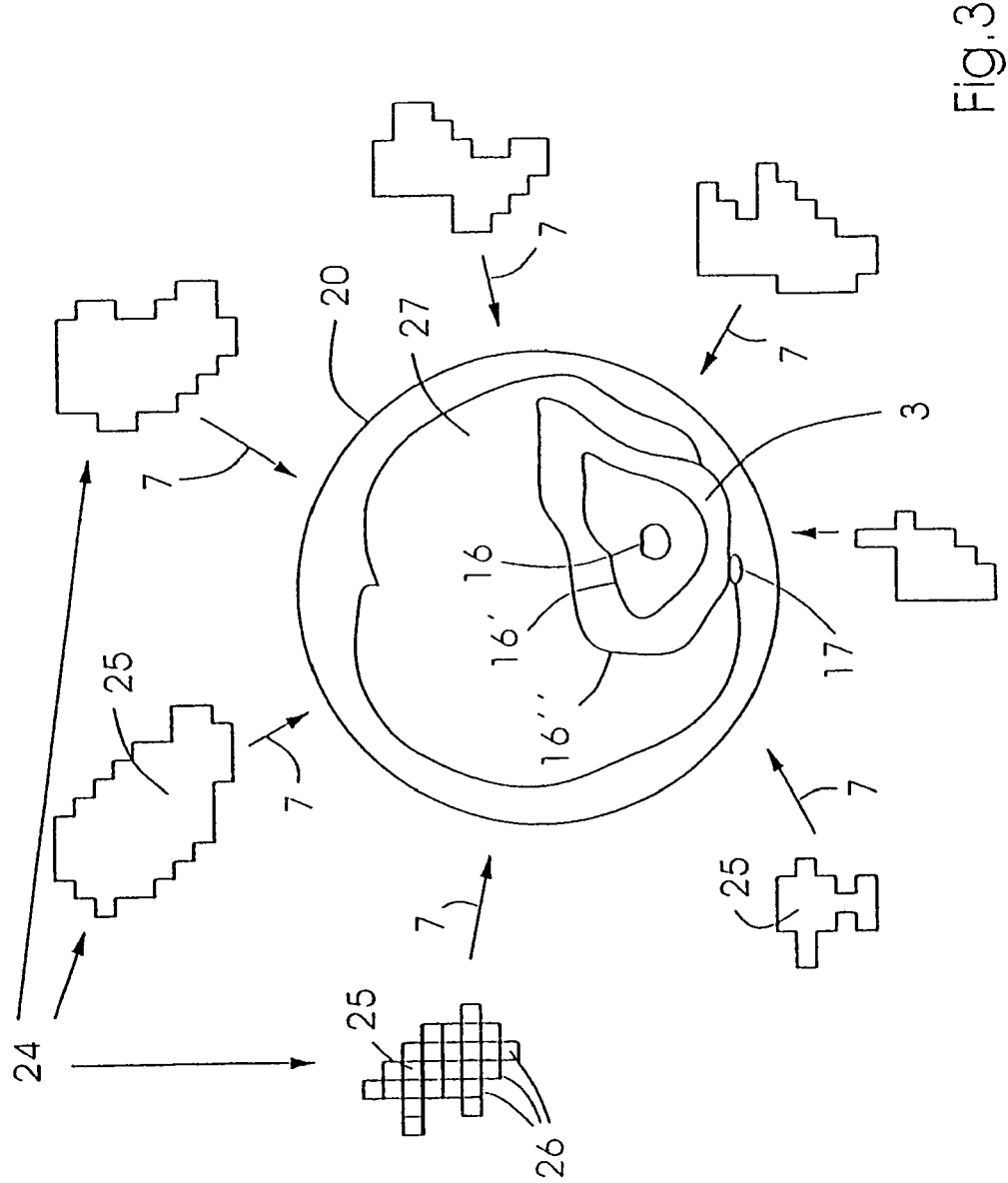
FIG. 3 shows an explanation of the principle of optimum radiation to be verified in accordance with the invention.

In a second step, the field shape and the intensity distribution of the therapeutic beam 1 are measured and recorded during application of the therapeutic radiation fields 24 (FIG. 3). Thereby and on the basis of the current computer tomography data set, the radiation dose distribution 16, 16', 16" (FIG. 3) applied to the patient 21 can be reconstructed and verified online. In case of deviations, the irradiation can optionally be interrupted or continued with corresponding corrections. The type and arrangement of the X-ray source 10 and of the medium 13 for detecting the beams 1 and 4 permit monitoring of the relative position of structures (target volume 3, regions 16, 16', 16" of the target volume 3 to be irradiated with different doses, and endangered organs 17) with low contrast (soft tissue contrast) in the therapeutic radiation field 24 and its surrounding (FIG. 3) by means of the X-ray beam 4 during application of the individual therapeutic radiation fields 24 and performance of immediate and nearly simultaneous correction.

This requires continuous detection of the above-mentioned parameters, which is effected in accordance with the invention in the transmitting breaks of the high-energy beam 1 using the X-ray beam 4 and the medium 12 or 13 and can be directly taken into consideration for subsequent application. This detection is also included in the previously detected three-dimensional parameters to obtain exact verification and correction.

In an advantageous manner, the above-mentioned permanently taken "current recordings" of the target volume 3 detect three-dimensional parameters during transmitting breaks in the high-energy beam 1. This is possible by directing the X-ray beam 4 onto the target volume 3 from different directions during detection. In one embodiment, the radiation source 10 for the X-ray beam 11 is designed such that it can describe a circular motion in one plane about an axis 28 extending through the target volume 3 towards the radiation source 11 of the high-energy beam 1. This is not illustrated since the motion is very small and the directions 5, 6 of the beams 1, 4 remain substantially opposite to each other. Of course, the controller 15 (FIG. 2) must be designed such that it establishes a three-dimensional representation of the region of the target volume using the data of the X-ray recordings along this circular motion to use same for verification.

This circular motion, which is performed mostly in a small region, may be effected e.g. mechanically through eccentric arrangement of the radiation source 10 of the X-ray beam 4 on a rotary disc.

The above-mentioned "current recordings" can be limited to a critical region e.g. to a region where the tumor borders on an endangered organ.

Figure 2:
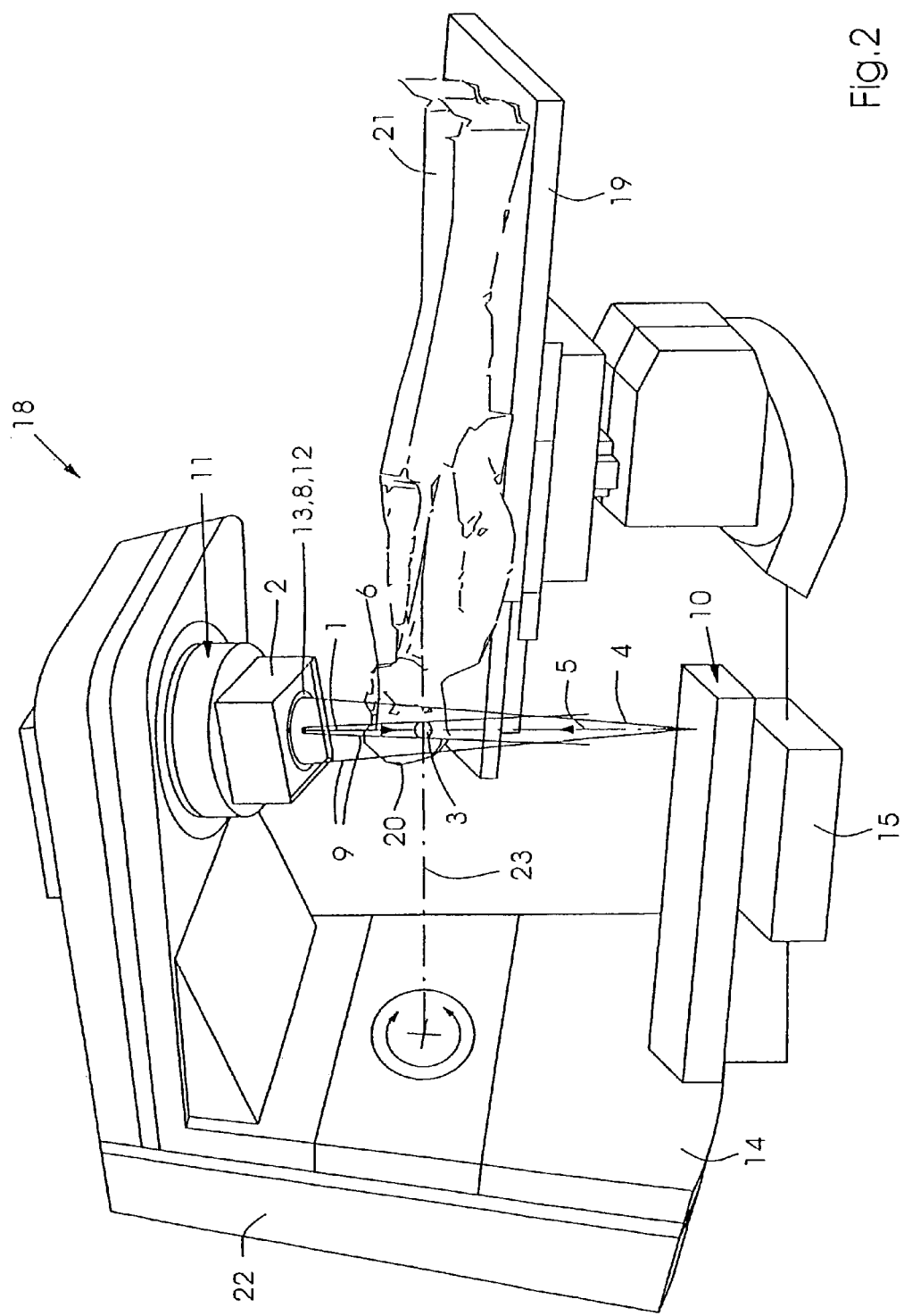
FIG. 2 shows an inventive device during use.

FIG. 2 shows an inventive device during use. This conventional construction of a radiation device 18 comprises a radiation source 11 for the therapeutic beam 1, a patient table 19 and a means 2 for radiation modulation to direct the medically indicated radiation onto a target volume 3, e.g. onto the head 20 of a patient 21 such that a tumor is maximally damaged and the surrounding tissue is protected to a maximum degree. Towards this end, a frame (gantry) 14 is provided which can surround the patient 21 from all sides. The gantry 14 contains the radiation source 11 for the therapeutic beam 1, with the high-energy radiation 1 being generated e.g. by a linear accelerator 22. The radiation source 10 for the X-ray beam 4 is disposed on the gantry 14 opposite to the radiation source 11, as previously described in FIG. 1. In this connection, reference is made to the above description, wherein identical reference numerals refer to components having identical functions.

The gantry 14 can be rotated about a horizontal axis of rotation 23, wherein the beams 1 and 4 are directed onto the target volume 3 or its surroundings. The target volume 3 is in the isocenter of the beams 1 and 4, wherein the radiation sources 11 and 10 and a means 2 for radiation modulation circulate around the axis 23 of the patient 21 during rotation of the gantry 14. At the same time, the treatment table 19 may be displaced or rotated to provide exact adjustment of the setting of the radiation of the therapeutic beam 1 onto the target volume 3 of the patient 21. The position of the patient 21 can thereby be corrected such that he/she is positioned in accordance with the treatment plan.

Through rotation of the gantry, the target volume 3 experiences maximized irradiation from the various irradiation directions 7 (FIG. 3), while the surrounding tissue is protected to a maximum extent, since it is exposed to the high-energy beams 1 only for a short time. Moreover, certain areas of the body, such as e.g. the spinal cord or other endangered organs 17, must be completely protected from the high-energy radiation 1 and are largely excluded by the design of the therapeutic radiation fields 24 from the various directions 7 (FIG. 3).

The position and the profile of the target volume 3 and the position of endangered organs 17 or of areas 16, 16', 16" which are provided for different radiation doses are detected by the medium 13 in three dimensions using the X-ray beam 4. At the same time, the actual state of the modelled therapeutic beam 1 is also detected and optionally corrected as described above. This data is processed such that the collimator 2 forms a corresponding collimator opening, with which the exact shape of the target volume 3 can be irradiated with the desired radiation dose distribution 16, 16', 16" (FIG. 3) through the inventive detection and verification. Using collimator 2, the radiation dose distribution 16, 16',

16" is obtained through application of one or more therapeutic radiation fields 24 of various duration from several directions 7.

To be able to obtain any setting, a controller 15 is provided which may be a specially designed or universally usable computer. The controller 15 is provided with the treatment plan and is connected to media 8 and 12 for recording the data to be processed and for control of the above-mentioned processing, to the medium 13 for detecting the beams 1 and 4, to the means 2 for modulation of the high-energy beam 1, to a drive for setting the position of the patient table 19 and to radiation sources 10 and 11 and to a drive and a position detection means for the gantry 14. It is operated in correspondence with the inventive control method, e.g. using the inventive computer program. The radiation source 11 and the means 2 for radiation modulation, the gantry 14, and optionally also the patient table 21 are controlled on the basis of the irradiation plan and the above-described repeated verification. The means 2 may be a collimator or a scanner. The therapeutic radiation fields 24 to be irradiated are defined by the collimator or generated through scanning of a therapeutic beam 1.

FIG. 3 illustrates the principle of tumor irradiation, wherein a medically indicated high-energy radiation 1 is applied from different directions 7. For optimum irradiation of a target volume 3, e.g. a tumor as mentioned above, and maximum protection of the bordering tissue, various therapeutic radiation fields 24 are formed for each of the different radiation directions 7. This is provided by the means 2 for radiation modulation which may be designed as a collimator or scanner. To assure that the target volume 3 to be irradiated receives the required dose while endangered organs 17 are protected, the therapeutic radiation fields 24 may e.g. be formed as matrices 25 of individual fields 26 with different radiation doses. Other possibilities, such as continuous scanning, are also feasible. Such matrices 25 can be reproduced in almost any shape through leaf adjustments of a multi-leaf collimator, wherein thin leaves obtain an optimum fine reproduction of the therapeutic radiation fields 24. In addition to the example shown, several different therapeutic radiation fields 24 of different duration may be applied to obtain regions 16, 16', 16" with different radiation doses in an optimum manner. In this process, the inventive, nearly simultaneous verification and correction takes place in the above-described manner i.e. with repetitive verification which is frequently performed for each radiation direction 7.

The figures represent only examples of the invention. The therapeutic radiation fields 24 can also be generated by a scanner instead of a collimator. The scanner then serves as means 2 for radiation modulation and the medium 8 or 13 must detect the scanned therapeutic radiation fields 24 such that the inventive verification and correction, including optional interruption of treatment, can be effected in an appropriate manner. Other designs are also feasible, which utilize the basic idea of the invention.

LIST OF REFERENCE NUMERALS 1 high-energy modulated beam (therapeutic beam)
2 means for beam modulation
3 target volume
4 X-ray beam
5 direction of the X-ray beam
6 direction of the high-energy beam
7 different directions of detection and irradiation of the target volume
8 medium for detecting the high-energy modulated beam
9 path of rays
10 radiation source for X-ray beam
11 radiation source for high-energy beam
12 medium for detecting the X-ray beam
13 medium for detecting the high-energy beam and X-ray beam
14 gantry
15 controller (computer)
16,16',16" regions of different radiation doses (radiation dose distribution)
17 endangered organs (e.g. spinal cord)
18 radiation device
19 patient table
20 head
21 patient
22 linear accelerator
23 axis of rotation of gantry
24 therapeutic radiation fields
25 matrices
26 individual fields
27 brain
28 axis which extends through the target volume to the radiation source of the high-energy beam

I claim:

1. A device for performing and verifying therapeutic irradiation, the device having a radiation source for a high-energy beam and means for modulating the high-energy beam on a gantry of an irradiation device, wherein, for verification, a radiation source of an X-ray beam is disposed on a side of a target volume opposite to the radiation source for the high-energy beam such that a direction of the X-ray beam is substantially opposite to a direction of the high-energy beam, wherein a medium for detecting the X-ray beam and for detecting the high-energy beam is disposed between the radiation source for the high-energy beam and the target volume, the medium being designed to detect regions of different radiation doses of the high-energy beam, the device also having a controller connected to the medium for detecting the high-energy and X-ray beams, to the modulating means for the high-energy beam, to a drive for adjusting a position of a patient table, and to the radiation sources for the X-ray and high-energy beams, wherein the controller can be loaded with a treatment plan to control the device, the device comprising:

means for detecting an anatomy and a position of the patient in a region of the target volume via the X-ray beam by directing the X-ray beam onto the region from various directions before application of the high-energy beam;

means for comparing the detected anatomy and position of the patient to the treatment plan and for correcting the patient position and/or treatment plan, if necessary;

means for applying the high-energy beam from a radiation direction and for detecting a shape and area of various radiation doses thereof;

means for detecting at least one partial region of the target volume including an immediate vicinity thereof using the X-ray beam during an irradiation pause of the high-energy beam;

means for comparing an X-ray recording with a detected applied high-energy beam and for correcting the treatment plan, if necessary;

means for iterative repetition until a process prescribed by the treatment plan is completed for said radiation direction; and means for repeatedly changing said radiation direction as prescribed by the treatment plan.

2. The device of claim 1, further comprising means for directing the X-ray beam, during irradiation pauses of the high-energy beam, onto at least one partial region of the target volume, including an immediate vicinity thereof, from various directions and within a region which is sufficiently small to remain substantially opposite to a direction of the high-energy beam in order to examine a detection region in three dimensions using data detected from various directions and for verification in real time.

3. The device of claim 2, wherein the radiation source for the X-ray beam is designed to describe a circular motion in a plane which is disposed about an axis extending through the target volume towards the radiation source of the high-energy beam.

4. The device of claim 1, wherein the controller is designed to consider a shape and position of endangered organs during verification and correction of modulation of the high-energy beam.

5. The device of claim 1, wherein the X-ray beam can detect a partial region of the target volume together with an adjacent region of an endangered organ during irradiation pauses of the high-energy beam for verification in real time.

6. The device of claim 1, wherein the controller is structured to establish a protocol of applied radiation.

7. The device of claim 6, wherein the controller is structured to establish a protocol in three-dimensional space.

8. The device of claim 1, wherein the controller is structured to establish a protocol concerning corrections of the treatment plan for performed irradiation.

9. The device of claim 1, wherein the medium comprises a first medium for detecting the high-energy beam and a second medium for detecting the X-ray beam.

10. The device of claim 9, wherein at least one of said first medium and said second medium comprises an array of photo diodes which consist essentially of amorphous material.

11. The device of claim 10, wherein said photo diodes are disposed in a housing which only slightly attenuates the high-energy beam.

12. A computer program for controlling a device for carrying out and verifying therapeutic irradiation using a high-energy beam, the high-energy beam being modulated by a means for radiation modulation, wherein, for verification, an X-ray beam is directed onto a target volume in a direction substantially opposite to that of the high-energy beam in order to detect the target volume, and the X-ray beam, is detected, relative to its direction, behind the target volume to produce an image thereof, wherein the high-energy beam is detected in front of the target volume, the program being structured to control the device using a continuer executing the following steps:
  a) spatially detecting an anatomy and position of a patient in a region of the target volume via the X-ray beam by directing same onto said region from various directions before application of the high-energy beam;
  b) comparing the detected anatomy and position of the patient with a treatment plan and correcting the patient position and/or treatment plan if necessary;
  c) applying the high-energy beam from a first direction and detecting a shape and area of various radiation doses thereof;
  d) detecting at least one partial region of the target volume, including a direct vicinity thereof, using the X-ray beam during an irradiation pause of the high-energy beam;
  e) comparing an X-ray recording extracted in step d) with detection of the applied high-energy beam extracted in step c) and correcting the treatment plan, if necessary;
  f) repeating steps c), d), and e) until an application prescribed by the treatment plan is completed for the first radiation direction; and
  g) repeating steps c) through f) for all radiation directions prescribed by the treatment plan.

13. The computer program of claim 12, wherein the program is designed to control the X-ray beam from different directions during irradiation pauses of the high-energy beam, wherein these directions move within a range which is sufficiently small that the X-ray beam direction is still substantially opposite to a direction of the high-energy beam and impinges on at least one partial region of the target volume including an immediate vicinity thereof for verification in three dimensions and in real time using data detected from different directions.

14. The computer program of claim 12, wherein data is obtained by causing a radiation source for the X-ray beam to describe a circular motion in a plane which is disposed about an axis extending through the target volume and towards a radiation source of the high-energy beam.

15. The computer program of claim 12, wherein the program is designed to analyse a shape and position of endangered organs for verification and correction of modulation of the high-energy beam.

16. The computer program of claim 12, wherein a partial region of the target volume, including a bordering region of an endangered organ, is detected by the X-ray beam in irradiation pauses of the high-energy beam and taken into consideration for verification in real time.

17. The computer program of claim 12, wherein the program is structured to establish a protocol concerning applied radiation.

18. The computer program of claim 12, wherein the program is structured to establish a protocol concerning corrections to the treatment plan for performed irradiation.

19. A control method to operate a device for carrying out and verifying therapeutic irradiation using a high-energy beam modulated by a means for radiation modulation, wherein, for verification, an X-ray beam is directed onto a target volume in a substantially opposite direction with respect to that of the high-energy beam to detect the target volume, wherein the X-ray beam is detected behind the target volume to effect an image thereof and the high-energy beam is detected in front of the target volume, the method comprising the following steps:
  a) spatially detecting an anatomy and position of the patient in a region of the target volume using the X-ray beam by directing same onto said region from various directions and before application of the high-energy beam;
  b) comparing a detected anatomy and position of a patient with a treatment plan and correcting the patient position and/or the treatment plan, if necessary;
  c) applying the high-energy beam from a first direction to detect a shape a thereof and regions of various radiation dosage;
  d) detecting at least one partial region of the target volume, including its direct vicinity, using the X-ray beam and during an irradiation pause of the high-energy beam;
  e) comparing an X-ray recording of step d) with a detected applied high-energy beam of step c) to correct the treatment plan, if necessary;

f) repeating steps c), d), and e) until an application prescribed by the treatment plan is completed for the first radiation direction;

g) repeating steps c) through f) for all radiation directions prescribed by the treatment plan.

20. The control method of claim 19, wherein the X-ray beam is directed, from different directions within a region which is sufficiently small that it is still substantially opposite to a direction of the high-energy beam, onto at least one partial region of the target volume including an immediate vicinity thereof and during irradiation pauses of the high-energy beam to detect parameters in three dimensions for verification in real time using data detected from various directions.

21. The control method of claim 20, wherein the data is obtained by causing a radiation source for the X-ray beam to describe a circular motion in a plane which is disposed about an axis which extends through the target volume and towards a radiation source for the high-energy beam.

22. The control method of claim 19, wherein a shape and position of endangered organs are taken into consideration for verification and correction of modulation of the high-energy beam.

23. The control of claim 19, wherein the X-ray beam can detect a partial region of the target volume having a bordering region of an endangered organ during irradiation pauses of the high-energy beam for verification in real time.

24. The control method of claim 19, wherein a protocol is established of applied radiation.

25. The control method of claim 19, wherein a protocol is established concerning corrections to the treatment plan for performed radiation application.

* * * * *